United States Patent
Andersen et al.

(10) Patent No.: US 6,988,613 B2
(45) Date of Patent: Jan. 24, 2006

(54) COMPOSITION FOR IVF

(75) Inventors: Tina Meinertz Andersen, Horsholm (DK); Lars Klingberg Muller, Ballerup (DK)

(73) Assignee: Novo Nordisk A/S, Bagsværd (DK)

( * ) Notice: Subject to any disclaimer, the term of this patent is extended or adjusted under 35 U.S.C. 154(b) by 105 days.

(21) Appl. No.: 10/068,224

(22) Filed: Feb. 5, 2002

(65) Prior Publication Data
US 2002/0166789 A1 Nov. 14, 2002

Related U.S. Application Data

(60) Provisional application No. 60/273,162, filed on Mar. 2, 2001.

(30) Foreign Application Priority Data

Feb. 6, 2001 (DK) ............... 2001 00189
Mar. 8, 2001 (DK) ............... 2001 00382

(51) Int. Cl.
*B65D 85/21* (2006.01)
*B65B 31/02* (2006.01)

(52) U.S. Cl. ............... 206/213.1; 53/403; 53/405; 53/408; 53/428; 53/432; 206/524.8

(58) Field of Classification Search ............... 53/432, 53/434, 403–408, 428; 206/204, 205, 213.1, 206/438, 524.8, 528, 531, 532, 534, 538, 206/539, 540; 514/1
See application file for complete search history.

(56) References Cited

U.S. PATENT DOCUMENTS

| 6,177,420 B1 * | 1/2001 | Leemhuis et al. ............ 514/183 |
| 6,258,320 B1 * | 7/2001 | Persing et al. ................ 422/40 |

FOREIGN PATENT DOCUMENTS

| EP | 0 259 949 A2 | 3/1988 |
| WO | WO 90/03429 | 4/1990 |
| WO | WO 98/28323 | 7/1998 |
| WO | WO 01/19354 A2 | 3/2001 |

* cited by examiner

*Primary Examiner*—Jim Foster
(74) *Attorney, Agent, or Firm*—Len S. Smith; Reza Green; Richard Bork

(57) ABSTRACT

A solid, stable composition containing a meiosis activating substance can be prepared by adding a protein or a phosphoglycid in the presence of an atmosphere having a low content of oxygen, for example in vacuo.

11 Claims, No Drawings

COMPOSITION FOR IVF

CROSS REFERENCE TO RELATED APPLICATIONS

This application claims priority under 35 U.S.C. 119 of Danish application no. PA 2001 00189 filed on Feb. 6, 2001, Danish application no. PA 2001 00382 filed on Mar. 8, 2001 and U.S. provisional application no. 60/273,162 filed on Mar. 2, 2001, the contents of which are fully incorporated herein by reference.

The present invention relates to a solid, chemically stable composition that can be used in connection with in vitro fertilisation or in vitro maturation (hereinafter designated IVF or IVM, respectively). More specifically, it relates to a container containing such a solid composition.

BACKGROUND OF THIS INVENTION

Several meiosis activation substances (hereinafter designated MAS) are known. When MAS are kept in a medium containing oocytes, the oocytes become more prone to fertilisation. However, a major problem with the use of MAS is that, usually, they have a very low solubility and low chemical stability under the conditions at which they are to be stored and used.

The object of this invention is to overcome or ameliorate at least some of the disadvantages of the prior art. Hence, not all the more detailed objects mentioned below may be fully overcome or ameliorated.

One object of this invention is to develop a composition containing MAS or a derivative thereof that can be dissolved in an aqueous medium in a sufficient concentration to be used for IVF or IVM.

Another object is to develop a composition containing MAS or a derivative thereof which can be dissolved in an aqueous medium without any physical influence such as heating, stirring, or ultrasound treatment.

A third object is to develop a composition containing MAS or a derivative thereof which has a sufficient chemical and physical stability at the conditions under which it is stored and used.

The solubility of a preferred MAS, i.e., FF-MAS, in water is very low, i.e., approximately 20 picogram/ml (corresponding to $2\times10^{-5}$ µg/ml). In ethanol, the solubility of FF-MAS is substantially higher, i.e., approximately 12 mg/ml. According to our preliminary investigations, the highest solubility of FF-MAS in a mixture of ethanol and water (1:2.5) is approximately 0.4 mg/ml. Several other MASs have a similar low solubility in water.

DETAILED DESCRIPTION OF THIS INVENTION

Surprisingly, it has been found that the stability of MAS can be improved when it is stored in the absence of oxygen or in the presence of only a minor amount of oxygen. Hence, one embodiment of this invention relates to a closed container having a low content of oxygen and further containing MAS. According to a preferred embodiment, this invention relates to a closed container, wherein the content of oxygen is below about 0.01 mole oxygen per liter container volume, preferably below about 0.001 mole oxygen per liter container volume, even more preferred below about 0.0001 mole oxygen per liter container volume.

Furthermore, surprisingly it has now been found that a solid composition containing MAS and an additive has a good solubility in water. The additives are components which, when added to MAS, provides a composition which can be used to prepare an aqueous solution containing MAS wherein the concentration of MAS is sufficiently high, preferably above about 1 µg/ml.

Hence, another embodiment of this invention relates to a closed container having a low content of oxygen and further containing a solid composition with high aqueous solubility comprising MAS and an additive. According to a preferred embodiment, this invention relates to a closed container containing an atmosphere having a low content of oxygen and further containing a solid composition with high aqueous solubility comprising MAS and an additive.

According to a further embodiment, this invention relates to a container, wherein the content of oxygen in the atmosphere is below about 10%, preferably below about 5%, more preferred below about 1% (volume/volume). According to a still further embodiment, this invention relates to a container, wherein a substantial part of the atmosphere is nitrogen or argon.

According to a still further embodiment, this invention relates to a container, wherein the content of nitrogen or argon in the atmosphere is above about 90%, preferably above about 95%, more preferred above about 99% (volume/volume).

Examples of preferred additives are water-soluble proteins such as serum albumin, e.g., human serum albumin (hereinafter designated HSA), optionally in recombinant form, enzymes and phosphoglycerides such as phosphatidylethanolamin, phosphatidylcholine, phosphatidylserine, and phosphatidylnositol. As is known by the skilled art worker, albumin can, for example, be prepared from serum or by genetic engineering (recombinant) and, consequently, the products prepared can be designated serum albumin or recombinant albumin, respectively.

According to one embodiment, this invention relates to a container, wherein the additive is a protein or a phosphorglycerid, preferably serum albumin, most preferred human serum albumin, optionally in recombinant form. According to a further embodiment, this invention relates to a container, wherein the additive is serum albumin, optionally in recombinant form. According to a still further embodiment, this invention relates to a container, wherein the additive is human serum albumin, optionally in recombinant form. According to a still further embodiment, this invention relates to a container, wherein the content of additive in the solid compositions is above about 90%, preferably above about 95%, even more preferred above about 98%, and most preferred above about 99%.

Preferably, the solid compositions have a content of water below about 10%, preferably below about 5%, more preferred below about 1% (weight/weight). According to a preferred embodiment, this invention relates to a container, wherein the content of water in the solid composition is below about 10%, preferably below about 5%, more preferred below about 1% (weight/weight).

Preferably, the solid compositions have a content of organic solvent below about 10%, preferably below about 5%, more preferred below about 1% (weight/weight). According to a preferred embodiment, this invention relates to a container, wherein the content of organic solvent in the solid composition is below about 10%, preferably below about 5%, more preferred below about 1%.

Preferably, the solid compositions have a content of MAS below about 1%, preferably below about 0.1%, more preferred below about 0.05% (weight/weight). According to a preferred embodiment, this invention relates to a container, wherein the content of MAS in the solid composition is below about 10%, preferably below about 5%, more preferred below about 2%, most preferred below about 1% (weight/weight).

Preferably, the solid compositions have a content of additive above about 50%, preferably above about 80%, even more preferred above about 99%, and most preferred above about 99.9%.

Preferably the weight ratio between MAS and the additive is in the range from about 1:10, preferably from about 1:50, to about 1:5,000. A preferred range is about 1:1000.

Preferred solid compositions are such which can be treated with an aqueous medium containing no or only low concentrations of organic solvent resulting in a solution having a sufficiently high concentration of MAS, e.g., above about 0.001 μg/ml, preferably above about 1 μg/ml. Preferably, these aqueous media contain below about 1%, preferably below about 0.5%, more preferred below about 0.1% of organic solvent (weight/weight). Earlier, several attempts to prepare compositions fulfilling this requirement have failed.

Herein, the term MAS designates compounds which mediate the meiosis of oocytes. More specifically, MASs are compounds which in the test described in Example 1 below has a percentage germinal vesicle breakdown (hereinafter designated GVB) which is significantly higher than the control. Preferred MASs are such having a percentage GVB of at least 50%, preferably at least 80%. Examples of MASs are mentioned in WO 96/00235, 96/27658, 97/00884, 98/28323, 99/58549, 99/67273, 98/52965, 98/55498, 99/32506, WO 00/35938, WO 00/35938, WO 00/53618, WO 98/54965, and EP 1250108.6, more specifically in Claim 1 thereof and the specific compounds mentioned therein. The above patent specifications giving specific examples of MASs and the corresponding U.S. patent applications and patents issued from them are incorporated by reference. For example, all the compounds mentioned specifically in the above patent specifications giving specific examples of MASs and the corresponding U.S. patent applications and patents issued from them are incorporated by reference. Examples of preferred MASs are all the compounds mentioned specifically in the above patent specifications giving specific examples of MASs and the corresponding U.S. patent applications and patents issued from them. Examples of especially preferred MASs are 4,4-dimethyl-5α-cholesta-8,14,24-triene-3β-ol (hereinafter designated FF-MAS); 4,4-dimethyl-5α-cholesta-8,14,24-trien-3,β-ol hemisuccinate; 5α-cholest-8,14-dien-3β-ol; 5 α-cholest-8,14-dien-3β-ol hemisuccinate; (20S)-cholest-5-en-3β,20-diol; 3β-hydroxy-4,4-dimethyl-5α-chola-8,14-dien-24-oic acid-N-(methionine) amide; cholest-5-en-16β-ol; and (20S)-20-[(piperidin-1-yl)methyl]-4,4-dimethyl-5α-pregna-8,14-dien-3β-ol. According to a preferred embodiment, this invention relates to a container, wherein the MAS is 4,4-dimethyl-5α-cholesta-8,14,24-triene-3β-ol; 4,4-dimethyl-5α-cholest-8,14,24-trien-3β-ol hemisuccinate; 5α-cholest- 8,14-dien-3β-ol; 5α-cholest-8,14-dien-3β-ol hemisuccinate; (20S)-cholest-5-en-3β,20-diol; 3β-hydroxy-4,4-dimethyl-5α-chola-8,14-dien-24-oic acid-N-(methionine)amide; cholest-5-en-16β-ol; and (20S)-20-[(piperidin-1-yl)methyl]-4,4-dimethyl-5α-pregna-8,14-dien-3β-ol.

Generally, the solid composition is prepared in a manner known per se.

One way of preparing the solid compositions is to prepare a solution of MAS in an organic solvent such as ethanol and, then, to prepare an aqueous solution of the additive. Thereafter, the two solutions are mixed. After mixing the two solutions, the solvent is evaporated or allowed to evaporate. The evaporation can be accelerated by using continuous airflow over the mixed solutions, vacuum drying, freeze drying or any other feasible methods generally known to remove the solvent. Preferably, all these process steps are performed in the absence of oxygen or in the presence of only a minor amount of oxygen. Similarly, the final solid composition is kept in an atmosphere containing no or only a minor amount of oxygen. A preferred way of doing this is to store the solid composition in a closed container wherein the atmosphere has a low content of oxygen, e.g., in nitrogen or argon. These containers may be glass containers or containers of plastic having no undesired action on the solid composition. Preferred examples of such containers are capped vials, capouls, sealed dishes for IVF or IVM treatment or other sealed containers. Another preferred way of avoiding the contact with oxygen is to store the solid composition in a closed container in vacuo. For example, the containers can be sealed at the end of the freeze drying procedure.

The containers of this invention are filled with the atmosphere and the solid composition mentioned in the claims below in a manner known per se. Alternatively, there is vacuum in the containers of this invention.

According to one embodiment, this invention relates to a process for preparing a closed container having a low content of oxygen and further containing a solid composition comprising MAS and an additive, by preparing a solid composition comprising MAS and an additive by freeze drying and by closing the container in vacuo.

According to another embodiment, this invention relates to a process for preparing a closed container containing an atmosphere having a low content of oxygen and further containing a solid composition comprising MAS and an additive by preparing a solid composition comprising MAS and an additive, by filling the solid composition in a container, by, before, during or after step b), filling the container with an atmosphere having a low content of oxygen, and by closing the container.

According to a preferred embodiment, this invention relates to process, wherein the preparation of the solid composition comprising MAS and an additive is performed under conditions where there is a low concentration of oxygen, preferably in an atmosphere having a low content of oxygen. According to another, preferred embodiment, this invention relates to process, wherein the preparation of the solid composition comprising MAS and an additive is performed in vacuo.

The product marketed could be a delivery system having one or more depressions or hollows. Hereinafter, these depressions and hollows are mutually designated hollows. At least one of these hollows contains a solid composition and, in the same hollow, the atmosphere has a low content of oxygen, e.g., is nitrogen or argon, or is vacuum. A convenient way of placing the solid MAS therein is first to place a solution containing MAS and the additive in the hollow and thereafter to evaporate the solution, preferably in an atmosphere having a low content of oxygen, e.g., in nitrogen or argon, or in vacuum. In this way, the evaporation residue, i.e., the solid composition, is placed directly in the hollow in said device (delivery system).

According to one embodiment, this invention relates to a container which is a device having one or more hollows among which at least one of the hollows contains an atmosphere with a low content of oxygen and the solid composition. Alternatively, there is vacuum in the container.

Since the solid compositions are to be used for the treatment of oocytes, it is important that the solid compositions do not contain constituents that influence the oocytes negatively.

According to another embodiment, this invention relates to a container containing a solid composition that can be used for preparing an aqueous solution with the characteristics mentioned in any of the following preferred embodiments. According to a preferred embodiment, this invention relates to a container containing a solid composition that can be used for preparing an aqueous solution which when used for the treatment of oocytes can result in a percentage germinal vehicle breakdown (GVB) of at least 50%, preferably at least 80%, when MAS is FF-MAS. According to a preferred embodiment, this invention relates to a container containing a solid composition from which, when an aqueous media is added to the solid composition, a solution containing MAS in a concentration of above about 0.001 µg/ml, preferably above about 0.01 µg/ml, more preferred above about 0.1 µg/ml, even more preferred above about 1.0 µg/ml, and most preferred about 10 µg/ml, and even more preferred about 100 µg/ml, can be obtained. According to a preferred embodiment, this invention relates to a container containing a solid composition from which, when an aqueous media is added to the solid composition, a solution containing MAS in a concentration of below about 0.1 g/ml, preferably below about 0.01 g/ml, can be obtained. According to a preferred embodiment, this invention relates to a container containing a solid composition from which, when water is added to the solid composition, an aqueous solution wherein the content of organic solvent is below about 0.1%, preferably below about 0.05%, most preferred below about 0.01%, can be obtained.

One way of using the solid compositions is to dissolve the composition in an aqueous medium such as water and then, if desired, to add other constituents that may have a favourable influence on the maturation of the oocytes.

Another way of using the composition is to dissolve it in a media normally used for IVF or IVM.

The mentioning herein of a reference is no admission that it constitutes prior art.

Herein, the word "comprise" is to be interpreted broadly meaning "include", "contain" or "comprehend" (vide, the EPO guidelines C 4.13).

The present invention is further illustrated by the following examples which, however, are not to be construed as limiting the scope of protection. The features disclosed in the foregoing description and in the following examples may, in any combination thereof, be material for realising the invention in diverse forms thereof.

EXAMPLE 1

Method used for determining whether a compound is a MAS or not.

Oocytes were obtained from immature female mice (C57BL/6J×DBA/2J F1, Bomholtgaard, Denmark) weighing 13–16 grams, that were kept under controlled temperature (20–22° C.), light (lights on 06.00–18.00) and relative humidity (50–70%). The mice received an intraperitoneal injection of 0.2 ml gonadotropins (Gonal-F, Serono) containing 20 IU FSH and 48 hours later the animals were killed by cervical dislocation. The ovaries were dissected out and the oocytes were isolated in Hx-medium (see below) under a stereo microscope by manual rupture of the follicles using a pair of 27 gauge needles. Spherical oocytes displaying an intact germinal vesicle (hereinafter designated GV) were divided in cumulus enclosed oocytes (hereinafter designated CEO) and naked oocytes (hereinafter designated NO) and placed in α-minimum essential medium (α-MEM without ribonucleosides, Gibco BRL, Cat. No. 22561) supplemented with 3 mg/ml bovine serum albumin (BSA, Sigma Cat. No. A-7030), 5 mg/ml human serum albumin (HSA, State Serum Institute, Denmark), 0.23 mM pyruvate (Sigma, Cat. No S-8636), 2 mM glutamine (Flow Cat. No. 16-801), 100 IU/ml penicillin and 100 µg/ml streptomycin (Flow, Cat No. 16-700). This medium was supplemented with 3 mM hypoxanthine (Sigma Cat. No. H-9377) and designated Hx-medium.

The oocytes were rinsed three times in Hx-medium and oocytes of uniform size were divided into groups of CEO and NO. CEO and NO were cultured in 4-well multidishes (Nunclon, Denmark) in which each well contained 0.4 ml of Hx-medium and the compound to be tested in a concentration of 10 µM. One control well (i.e., 35–45 oocytes cultured in identical medium with no addition of test compound) was always cultured simultaneously with 3 test wells (35–45 oocytes per well supplemented with test compound).

The oocytes were cultured in a humidified atmosphere of 5% $CO_2$ in air for 24 hours at 37° C. By the end of the culture period, the number of oocytes with GV, GVB and polar bodies (hereinafter designated PB), respectively, were counted using a stereo microscope (Wildt, Leica MZ 12). The percentage of GVB, defined as percentage of oocytes undergoing GVB per total number of oocytes in that well, was calculated as:

% GVB=((number of GVB+number of PB)/total number of oocytes)×100.

EXAMPLE 2

Method used for determining whether a compound can be used as the additive in the solid compositions or not.

An additive for FF-MAS compositions are characterised by:

Improving the solubility of FF-MAS in ethanol/water (1:2.5 v/v)

Ensuring a clear solution of FF-MAS after reconstitution of the composition in MEM Alpha Medium.

Securing percent GVB is at least 50% preferable 80% when tested on oocytes obtained from immature female mice.

Prepare a saturated ethanolic solution of FF-MAS. Blend with an aqueous solution of the additive in the ration 1:2.5. By visual inspection control that surplus FF-MAS is available in the solution. Rotate the solution for 24 hours at room temperature. Filter the solution through 0, 22 µm filter, determine the content of FF-MAS by HPLC and calculate the solubility. Transfer 350 µl to 4-well dish and evaporate to dryness at room temperature. Add 500 µl MEM ALPHA medium (Gibcobal). If a clear solution is obtained within half an hour, the composition is tested on oocytes obtained from immature female mice. % GVB obtained is at least 50%, preferable 80%, vide example 1.

EXAMPLE 3

Composition containing Human Serum Albumin (HSA).

FF-MAS was dissolved in ethanol (25 µg FF-MAS/ml ethanol). HSA is dissolved in water (1%). 100 µl of the above mentioned ethanol solution (corresponding to the amount of FF-MAS needed for one treatment) and 350 µl of the above-mentioned HSA solution were mixed in a glass vial. The resulting mixture of FF-MAS and HSA was evaporated to dryness by airflow of argon. After the liquid was evaporated, the vial was sealed by a rubber septum and the vial was placed at a temperature of 2–8° C. At the time for usage, 500 μl of freshly prepared IVM media was added to the residue in the vial and shaken calmly for 1–2 minutes. The IVM media used was TCM 199 with Earle's salts (Sigma) to which was added 0.8% HSA, 2 mM L-glutamine, 0.25 mM sodium pyrovate, 100 IU/ml penicillin G, and 100 microgram/ml streptomycin. The liquid was transferred to a 4-well dish and the composition was tested on oocytes obtained from immature female mice. Percentage GVB obtained, see below in Table 1.

The stability of the formulation, as well as the recovery of FF-MAS from the vials were continuously followed, see below in Table 2.

TABLE 1

GVB data for FF-MAS in combination with HSA
Content of HSA in each vial: 6 mg/ml

| Substance | Dose FF-MAS (μmol/l) | Number of oocytes | % GVB |
|---|---|---|---|
| Control | — | 35 | 14 |
| FF-MAS* | 10 | 35 | 43 |
| FF-MAS | 0.24 | 35 | 86 |
| FF-MAS | 0.48 | 33 | 88 |
| FF-MAS | 1.2 | 35 | 91 |
| FF-MAS | 2.4 | 34 | 97 |
| HSA-control | — | 33 | 9 |

*internal control dissolved in ethanol

TABLE 2

Stability of FF-MAS in combination with HSA
Content of FF-MAS in each vial: 10 μg/ml
Content of HSA in each vial: 5 mg/ml

| Storage Conditions | Months of Storage | Assay μg/ml | % Recovery |
|---|---|---|---|
| 5° C. | 2 months | 10, 15 | 101% |
|  | 3 months | 10, 3 | 103% |
| 25° C./ | 2 months | 9, 71 | 97% |
| 60% RH | 3 months | 9, 5 | 95% |

"RH" designates relative humidity.

EXAMPLE 4

Preparation

FF-MAS was dissolved in ethanol (20 μg FF-MAS/ml ethanol) and HSA was dissolved in water (1%). 100 μl of the above mentioned ethanol solution (corresponding to the amount of FF-MAS needed for one treatment) and 250 μl of the above-mentioned HSA solution were mixed and 350 μl of the combined liquid was aliquoted in a glass vials. The vials were placed at −80° C. for one night. All samples were thereafter freeze-dried at −45° C. for 16 hours followed by 8 hours freeze drying at −15° C. and 8 hours freeze drying at +25° C. Before the freeze dryer was opened all vials were automatically sealed with rubber septums by a pressure of nitrogen. The vials were closed with a capsule and placed at a temperature of 2–8° C. At the time for usage, 500 μl of freshly prepared IVM media was added to the residue in each vial and shaken calmly for 1–2 minutes. The IVM media used was the same as that which was used in example 3. The liquid was transferred to a 4-well dish and the composition was tested on oocytes obtained from immature female mice. Percentage GVB obtained, see below in Table 3. The recovery of FF-MAS from the vials was determined on HPLC to be about 105%, corresponding to 2.10 μg FF-MAS/vial.

TABLE 3

GVB data from 2 tests on FF-MAS + HSA
compared to internal control

| Substance | Dose FF-MAS (μmol/l) | Number of oocytes | % GVB |
|---|---|---|---|
| FF-MAS* | 10/10 | 27/41 | 85/83 |
| FF-MAS + HSA | 5/5 | 28/108 | 100/95 |

*Internal control, FF-MAS dissolved in ethanol

EXAMPLE 5

A comparison on the solubility of FF-MAS in solutions containing either recombinant human albumin (hereinafter designated r-HA) or HSA has been performed. The solutions were prepared as in example 4, with 2.5 mg HSA or r-HA in each vial together with 2 μg FF-MAS. The solutions were filtered through a 0.22 μm filter but not freeze-dried prior to analysis. The recovery data are listed in table 4 below.

TABLE 4

Recovery of FF-MAS from solutions prior to freeze-drying.

| EtOH:Water | FF-MAS + HSA | FF-MAS + r-HA |
|---|---|---|
| 1:2.5 | 62% | 37% |
| 1:5 | 90% | 59% |
| 1:12.5 | 90% | 85% |
| 1:25 | 76% | 66% |
| 1:50 | 81% | 46% |
| 1:100 | 75% | 24% |

As seen from Table 4, the ideal ratio between ethanol and water is about 1:12.5.

EXAMPLE 6

FF-MAS was dissolved in ethanol (77 μg FF-MAS/ml ethanol) and HSA or r-HA was dissolved in water (1%). 26 ml of the above mentioned ethanol solution and 324 ml of the above-mentioned HSA solution or r-HA solution were mixed and 350 μl of the combined liquid was aliquoted in glass vials (corresponding to the amount of FF-MAS needed for one IVM treatment). The vials were placed at −35° C. for one night. All samples were thereafter freeze-dried at −30° C. for 16 hours followed by 8 hours freeze drying at −15° C. and 8 hours freeze drying at +25° C. Before the freeze dryer was opened all vials were automatically sealed with rubber septums in vacuo. The vials were closed with a capsule and stored for stability testing. At the time for usage, 500 μl of freshly prepared IVM media was added to the residue in each vial and shaken calmly for 1–2 minutes. The IVM media used was the same as that which was used in example 3. The results obtained are shown in table 5.

TABLE 5

|  | −18° C. | +5° C. | 25° C./ 60% RH | 40° C. |
|---|---|---|---|---|
| FF-MAS + HSA | No significant degradation after 6 months. | No significant degradation after 6 months. | No significant degradation after 6 months. | No significant degradation after 6 months. |
| FF-MAS + r-HA | N/A | No significant degradation after 3 months. | N/A | N/A |

"RH" designates relative humidity.

EXAMPLE 7

In order to test the robustness of the formulation, bulk solutions with different ratios between FF-MAS and HSA has been prepared. The recovery of FF-MAS was determined on HPLC on the bulk solutions and none of the samples were freeze dried. The ratio between ethanol and water was kept at 1:12.5 in all samples. Results see Table 6, n=2 in all samples. The analyses were performed right after the preparation.

TABLE 6

|  | FF-MAS/ vial | HSA/ vial | Ratio FF-MAS: HSA | Content of FF-MAS in bulk | Found FF-MAS | Recovery |
|---|---|---|---|---|---|---|
| I | 50 µg | 2.5 mg | 1:50 | 143 µg/ml | 133 µg/ml | 93% |
| II | 10 µg | 2.5 mg | 1:250 | 29 µg/ml | 27.7 µg/ml | 96% |
| III | 1 µg | 2.5 mg | 1:2500 | 2.9 µg/ml | 2.61 µg/ml | 90% |
| IV | 0.1 µg | 2.5 mg | 1:25000 | 0.29 µg/ml | 0.29 µg/ml | 100% |

During the preparation a slight precipitation was observed in the solution containing the highest amount of FF-MAS (143 µg/ml), but as seen in table 6, the recovery of FF-MAS from all solutions was ≧90%, which is very satisfactory.

EXAMPLE 8

Test on mouse oocytes on formulations with FF-MAS and r-HA prepared as described in example 5 and subsequently freeze-dried as described in example 6 has been performed. Five tests were conducted and the results are listed in Table 7.

TABLE 7

GVB data from 5 tests on FF-MAS + r-HA compared to internal control

| Substance | Dose FF-MAS (µmol/l) | Number of tested oocytes | % GVB |
|---|---|---|---|
| FF-MAS* | 10 | 180 | 85 |
| FF-MAS + r-HA | 5 | 188 | 87 |

*Internal control, FF-MAS dissolved in ethanol

What is claimed is:

1. A composition comprising a meiosis activation substance in a container wherein the oxygen content in the container is less than about 0.01 moles oxygen per liter and the container is capable of maintaining the oxygen content.

2. The composition of claim 1, wherein the oxygen content is less than about 0.001 moles of oxygen per liter.

3. The composition of claim 1, wherein the oxygen content is less than about 0.0001 moles of oxygen per liter.

4. The composition of claim 1, wherein the meiosis activation substance is a compound exhibiting a percentage germinal vesicle breakdown which is 50% higher than a control.

5. The composition of claim 1, wherein the meiosis activation substance is 4,4-dimethyl-5α-cholesta-8,14,24-triene-3β-ol; 4,4-dimethyl-5α-cholest-8,14,24-trien-3β-ol hemisuccinate; 5α-cholest-8,14-dien-3β-ol; 5α-cholest-8,14-dien-3β-ol hemisuccinate; (20S)-cholest-5-en-3β,20-diol; 3β-hydroxy-4,4-dimethyl-5α-chola-8,14-dien-24-olc acid-N-(methionine)amide; cholest-5-en-16β-ol; or (20S)-20-[(piperidin-1-yl)methyl]-4,4-dimethyl-5α-pregna-8,14-dien-3β-ol.

6. A process for preparing a pharmaceutical composition in a closed container, comprising:
   a) preparing a solid composition comprising a meiosis activation substance and an additive;
   b) adding the solid composition to the container;
   c) freeze drying the composition; and
   d) closing the container in vacuo.

7. The process of claim 6, wherein the preparation of the solid composition is performed in vacuo.

8. The process according to claim 6, wherein the preparation of the solid composition is performed in an atmosphere having an oxygen content of less than about 0.01 moles per liter.

9. A process for preparing a pharmaceutical composition in a closed container comprising:
   a) preparing a solid composition comprising a meiosis activation substance and an additive;
   b) filling the solid composition into the container;
   c) filling the container with an atmosphere having an oxygen content of less than 10%; and
   d) closing the container.

10. The process of claim 9, wherein the solid composition is prepared in an atmosphere having an oxygen content of less than about 0.01 moles per liter.

11. A process for increasing the stability of a composition in a closed container comprising:
   a) preparing a solid composition comprising a meiosis activation substance having an oxygen content of less than about 0.01 moles per liter and an additive;
   b) filling the solid composition into the container;
   c) filling the container with an atmosphere having an oxygen content of less than 10%; and
   d) closing the container.

* * * * *